United States Patent
Eguchi et al.

(10) Patent No.: US 11,008,545 B2
(45) Date of Patent: May 18, 2021

(54) SPORULATION METHOD OF *BACILLUS* BACTERIUM

(71) Applicant: IDEMITSU KOSAN CO., LTD., Chiyoda-ku (JP)

(72) Inventors: Takanori Eguchi, Chiyoda-ku (JP); Yasuyuki Morishita, Chiyoda-ku (JP); Yuki Tsukagoshi, Chiyoda-ku (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 111 days.

(21) Appl. No.: 15/565,029

(22) PCT Filed: Apr. 8, 2016

(86) PCT No.: PCT/JP2016/061604
§ 371 (c)(1),
(2) Date: Oct. 6, 2017

(87) PCT Pub. No.: WO2016/163534
PCT Pub. Date: Oct. 13, 2016

(65) Prior Publication Data
US 2019/0048311 A1    Feb. 14, 2019

(30) Foreign Application Priority Data
Apr. 9, 2015  (JP) ................ JP2015-079951

(51) Int. Cl.
| | | |
|---|---|---|
| *C12N 3/00* | (2006.01) | |
| *C12N 1/20* | (2006.01) | |
| *C12R 1/11* | (2006.01) | |
| *C12R 1/085* | (2006.01) | |
| *C12R 1/09* | (2006.01) | |
| *C12R 1/10* | (2006.01) | |
| *C12R 1/125* | (2006.01) | |
| *C12R 1/12* | (2006.01) | |
| *C12R 1/07* | (2006.01) | |

(52) U.S. Cl.
CPC ............... *C12N 3/00* (2013.01); *C12N 1/20* (2013.01); *C12R 1/07* (2013.01); *C12R 1/085* (2013.01); *C12R 1/09* (2013.01); *C12R 1/10* (2013.01); *C12R 1/11* (2013.01); *C12R 1/12* (2013.01); *C12R 1/125* (2013.01)

(58) Field of Classification Search
None
See application file for complete search history.

(56) References Cited

U.S. PATENT DOCUMENTS 9,839,222 B2 * 12/2017 Villegas Escobar ... A01N 63/02

FOREIGN PATENT DOCUMENTS

| JP | 48-75720 A | 10/1973 |
|---|---|---|
| JP | 04-79879 A | 3/1992 |
| JP | 2000-217567 A | 8/2000 |
| JP | 2007-195542 A | 8/2007 |
| JP | 2007-236286 A | 9/2007 |
| JP | 2008-199980 A | 9/2008 |

OTHER PUBLICATIONS

Luna et al. Brazilian Journal of Chemical Engineering, 2002, vol. 19, No. 2, pp. 133-140.*
Sigma-Aldrich product sheet for "Yeast Extract"; retrived from https://www.sigmaaldrich.com/catalog/product/sial/07533?lang=en&region=US on Oct. 24, 2019, pp. 1-3.*
Priest et al. "A Numerical Classification of the Genus *Bacillus*", Journal of General Microbiology, 1988, 134, pp. 1847-1882.*
International Search Report dated Jun. 28, 2016, in PCT/JP2016/061604 filed Apr. 8, 2016.
Yoshiharu Wakisaka et al., "Formation of Crystalline δ-Endotoxin or Poly-β-Hydroxybutyric Acid Granules by Asporogenous Mutants of Bacillus thuringiensis", Applied and Environmental Microbiology, Jun. 1982, vol. 43, No. 6, pp. 1473-1480.
R.R. Farrera et al., Carbon: nitrogen ratio interacts with initial concentration of total solids on insecticidal Crystal Protein and Spore Production in Bacillus thuringiensis HD-73, Applied Microbiology Biotechnology, 1998, vol. 49, No. 6, pp. 758-765.
Extended European Search Report dated Jul. 20, 2018 in European Patent Application No. 16776700.3, 6 pages.
Chen, Z.-M., et al., "Greater Enhancement of *Bacillus subtilis* Spore Yields in Submerged Cultures by Optimization of Medium Composition through Statistical Experimental Designs", Applied Microbiology and Biotechnology, 2009, XP019778516, vol. 85 No. 5, pp. 1353-1360.
Monteiro, S.M., et al., "A Procedure for High-Yield Spore Production by *Bacillus subtilis*", Biotechnology Progress, vol. 21 No. 4, XP055226281, Jan. 1, 2005, pp. 1026-1031.
Soni, A., et al., "*Bacillus* Spores in the Food Industry: A Review on Resistance and Response to Novel Inactivation Technologies", Comprehensive Reviews in Food Science and Food Safety, vol. 15 No. 6, XP055490381, Nov. 2016, pp. 1139-1148.
Office Action dated Jan. 3, 2020, in Chinese Patent Application No. 201680020658.6, filed Apr. 8, 2016 (w/ English-language Translation).
Wang Jiwen et al., "Optimization of Spore Culture Conditions for Bacillus megaterium $C_2$", Chinese Agricultural Science Bulletin vol. 30, No. 36, 2014, pp. 155-160 (w/ partial English translation).
Guo Xia-li et al., "Optimization of Sporulation Conditions of *Bacillus subtilis*", Soil and Fertilizer Sciences in China, vol. 3, 2012, pp. 99-103 (w/ partial English Translation).
Monteiro, S.M.S.et al., "Enhanced Spore Production of Bacillus subtilis Grown in a Chemically Defined Medium", Advances in Microbiology, 4, 2014, pp. 444-454.
Tavares, Milene B., et al., "Bacillus subtilis Endospores at High Purity and Recovery Yields: Optimization of Growth Conditions and Purification Method", Curr Microbiol, 2013, vol. 66, pp. 279-285.

* cited by examiner

*Primary Examiner* — Vera Afremova
(74) *Attorney, Agent, or Firm* — Oblon, McClelland, Maier & Neustadt, L.L.P.

(57) ABSTRACT

A method of producing *Bacillus* spores comprising a step of culturing the *Bacillus* bacterium using a liquid medium having a C/N ratio (weight ratio of carbon content to nitrogen content) of greater than 4 and less than 9.5.

11 Claims, No Drawings

SPORULATION METHOD OF *BACILLUS* BACTERIUM

TECHNICAL FIELD

The present invention relates to a method of efficiently producing *Bacillus* spores.

BACKGROUND ART

*Bacillus* bacteria are used in various fields such as production of enzymes and useful substances, production of fermented foods, decomposition of organic substances, microbial pesticides and microbial fertilizers. In situations where such microbial pesticides, microbial fertilizers and the like are used, spores of *Bacillus* bacteria are commonly utilized. However, even strains that exert excellent performance for such applications have been difficult to commercialize without efficient sporulation ability.

Media frequently used for liquid culture of *Bacillus* bacteria include Nutrient Broth (DIFCO), Luria Bertani broth and Trypticase Soy Broth (Beckton Dickinson), but in these media, sufficient proliferation was not obtained and spore formation was hardly observed in some cases.

Patent Document 1 discloses a method of allowing for sporulation by carrying out culturing including a step of decreasing the dissolved oxygen concentration after proliferation. In certain *Bacillus* bacteria, however, it is difficult to efficiently allow for sporulation even by using the same technique. In addition, in this method, it is necessary to adjust stirring and ventilation conditions in the culturing step, which makes the manufacturing process complicated.

Patent Document 2 discloses a method of allowing for sporulation by continuing cultivation for a long period of time after the carbon source has been exhausted. However, this method is not suitable for actual production because the culturing cost will be high due to prolonged cultivation. In addition, in certain *Bacillus* bacteria, it is difficult to allow for sporulation even by using the same technique.

Patent Document 3 discloses a method of producing spores by defining the range of the phosphate concentration in the culture medium and the range of the oxygen supply and stirring rate as culture conditions. In certain *Bacillus* bacteria, however, it is difficult to efficiently form spores even by using the same technique. In addition, it is necessary to use a culture facility capable of achieving prescribed culture conditions in practice.

PRIOR ART REFERENCES

Patent Documents

Patent Document 1: Japanese Laid-open Patent Application (Kokai) No. 2007-236286
Patent Document 2: Japanese Laid-open Patent Application (Kokai) No. 2000-217567
Patent Document 3: Japanese Laid-open Patent Application (Kokai) No. 2007-195542

SUMMARY OF THE INVENTION

Problems to be Solved by the Invention

An object of the present invention is to provide a culturing method capable of efficiently producing spores of a *Bacillus* bacterium which hardly form spores in general liquid medium for bacteria.

Means for Solving the Problems

The present inventors intensively studied in order to solve the above problems, and consequently has found liquid medium compositions suitable for efficient proliferation and sporulation of *Bacillus* bacteria whose spore production efficiency is not sufficient in cultivation using conventional liquid media for bacteria, thereby completed the present invention.

The present invention is as follows:
[1] A method of producing *Bacillus* spores comprising a step of culturing the *Bacillus* bacterium using a liquid medium having a C/N ratio (weight ratio of carbon content to nitrogen content) of greater than 4.0 and less than 9.5.
[2] The method of producing *Bacillus* spores described in [1], wherein the C/N ratio in the liquid medium used for culturing is 4.5 or more and less than 9.5.
[3] The method of producing *Bacillus* spores described in [1], wherein the C/N ratio in the liquid medium used for culturing is 4.5 or more and 7.5 or less.
[4] The method of producing *Bacillus* spores described in [1], wherein the C/N ratio in the liquid medium used for culturing is 6.0 or more and 7.5 or less.
[5] The method of producing *Bacillus* spores described in any one of [1] to [4], wherein the carbon content in the liquid medium is 50 g/L or less.
[6] The method of producing *Bacillus* spores described in any one of [1] to [4], wherein the carbon content in the liquid medium is 25 g/L or less.
[7] The method of producing *Bacillus* spores described in any one of [1] to [6], wherein the potassium content in the liquid medium is less than 2.0 g/L.
[8] The method of producing *Bacillus* spores described in any one of [1] to [6], wherein the potassium content in the liquid medium is 1.9 g/L or less.
[9] The method of producing *Bacillus* spores described in any one of [1] to [8], wherein the carbon and nitrogen sources contained in the liquid medium are carbon and nitrogen sources which can be utilized by the *Bacillus* bacterium.
[10] The method of producing *Bacillus* spores described in [9], wherein the carbon source which can be utilized by the *Bacillus* bacterium is one or more carbon sources selected from the group consisting of starch, glucose, lactose, glycerol, arabinose, ribose, xylose, galactose, fructose, mannose, inositol, mannitol, sorbitol, glucosamine, N-acetylglucosamine, cellobiose, maltose, sucrose, trehalose, xylitol, alcohols, organic acids, organic salts, and alkanes; and the nitrogen source which can be utilized by the *Bacillus* bacterium is one or more nitrogen sources selected from the group consisting of soybean-derived components, yeast-derived components, corn-derived components, animal and plant proteins and hydrolysates thereof, and ammonium salts such as ammonium nitrate, ammonium sulfate, ammonium chloride, ammonium acetate, ammonia, sodium nitrate, potassium nitrate, sodium glutamate, urea and the like.
[11] The method of producing *Bacillus* spores described in any one of [1] to [10], wherein the *Bacillus* bacterium is *Bacillus simplex, Bacillus subtilis, Bacillus amyloliquefaciens, Bacillus pumilus, Bacillus megalerium, Bacillus thuringiensis, Bacillus popilliae, Bacillus cereus, Bacillus licheniformis, Bacillus firmus, Bacillus velezensis, Bacillus stearothermophihlus, Bacillus pichinotyi. Bacillus acidocaldarius, Bacillus alcalophilus, Bacillus alkalicola, Bacillus coagulans, Bacillus azotoformans, Bacillus anthracis, Bacillus siamensis, Bacillus badius, Bacillus bataviensis,*

*Bacillus brevis, Bacillus cycloheptanicus, Bacillus circulans, Bacillus aneurinilyticus, Bacillus migulanus, Bacillus abyssalis, Bacillus aestuarii, Bacillus polymyra,* or *Bacillus* sp.

[12] The method of producing *Bacillus* spores described in any one of [1] to [10], wherein the *Bacillus* bacterium is *Bacillus siamensis, Bacillus simplex* or *Bacillus megaterium*.

Effect of the Invention

The present invention can enable stable proliferation and sporulation of *Bacillus* bacteria, and further proliferation to higher concentration and sporulation at a higher rate.

Embodiments for Carrying Out the Invention

In the present invention, *Bacillus* bacteria are not particularly limited as long as they are bacteria classified as *Bacillus*, and include *Bacillus simplex, Bacillus subtilis, Bacillus amyloliquefaciens, Bacillus pumilus, Bacillus megaterium, Bacillus thuringiensis, Bacillus popilliae, Bacillus cereus, Bacillus licheniformis, Bacillus firmus, Bacillus velezensis, Bacillus stearothermophilus, Bacillus pichinotyi, Bacillus acidocaldarius, Bacillus alcalophilus, Bacillus alkalicola, Bacillus coagulans, Bacillus azotoformans, Bacillus anthracis, Bacillus siamensis, Bacillus badius, Bacillus bataviensis, Bacillus brevis, Bacillus cycloheptanicus, Bacillus circulans, Bacillus aneurinilyticus, Bacillus migulanus, Bacillus abyssalis, Bacillus aestuarii, Bacillus polymyxa,* or *Bacillus* sp.

Among these, *Bacillus simplex, Bacillus siamensis* and *Bacillus megaterium* are preferred.

In the present invention, a liquid medium having a C/N ratio (weight ratio of carbon content to nitrogen content) of greater than 4.0 and less than 9.5 is used for culturing. The C/N ratio is preferably 4.5 or more and less than 9.5, more preferably 4.5 or more and 7.5 or less, still more preferably 6.0 or more and 7.5 or less. The C/N ratio is calculated as follows:

C/N ratio=total carbon content in each media component/total nitrogen content in each media component.

The carbon content in the liquid medium used in the present invention is preferably 50 g/L or less, more preferably 25 g/L or less. On the other hand, the carbon content is preferably 3 g/L or more.

For carbon and nitrogen sources in the liquid medium used for culturing, those which can be utilized by *Bacillus* bacteria can be used. Examples of the carbon source capable of being utilized include sugars which can be utilized by *Bacillus* bacteria (such as starch, glucose, lactose, glycerol, arabinose, ribose, xylose, galactose, fructose, mannose, inositol, mannitol, sorbitol, glucosamine, N-acetylglucosamine, cellobiose, maltose, sucrose, trehalose, xylitol), alcohols, organic acids, organic salts, alkanes or other common carbon sources. Examples of the nitrogen source capable of being utilized include soybean-derived components, yeast-derived components, corn-derived components, animal and plant proteins and hydrolysates thereof, and ammonium salts such as ammonium nitrate, ammonium sulfate, ammonium chloride and ammonium acetate, ammonia, sodium nitrate, potassium nitrate, sodium glutamate, urea.

In the liquid medium used in the present invention, the potassium content is preferably less than 2 g/L, more preferably 1.9 g/L or less, in order to achieve a higher sporulation rate. The potassium content is preferably 0.2 g/L or more. As potassium sources, for example, at least one of soybean-derived component, yeast-derived component, corn-derived component, animal and plant proteins and hydrolysates thereof, $KH_2PO_4$, $K_2HPO_4$, and KCl are selected for culturing.

Other medium compositions, such as trace metal salts commonly used for culturing *Bacillus* bacteria, may be added as long as they do not adversely affect sporulation, and if necessary, for example, amino acids or vitamins may be added.

Culture conditions may be those generally used for liquid culture of *Bacillus* bacteria, including culture conditions at 20 to 40° C. under aerobic conditions (e.g., 15 to 50% oxygen concentration) with stirring for 10 to 100 hours. The pH of the medium is preferably 6.5 to 8.5, more preferably 7.0 to 8.0. Preculture may be performed before culturing in the liquid medium having the above-described C/N ratios.

In this way, *Bacillus* bacterial cells having a high sporulation rate (e.g., 50% or more, preferably 80% or more) can be obtained. Such *Bacillus* bacterial cells having a high sporulation rate can be used for a desired purpose after being subjected to proper operations such as concentration or removal of medium and drying.

EXAMPLES

The present invention will be described in detail below with reference to Examples, but is not limited to the following Examples.

Example 1

Evaluation of *Bacillus simplex* NBRC15720 Strain Using a 500 ml Erlenmeyer flask, each 100 ml of media containing glucose (Wako Pure Chemicals), defatted soy flour (Ajinomoto Healthy Supply), yeast extract (Difco), CSL (Corn Steep Liquor: ROQUETTE), peptone (Difco), and $KH_2PO_4$ (Wako Pure Chemicals) so that the final concentrations listed in Table 1 were achieved and further containing 100 ppm of $MnCl_2$ (Wako Pure Chemicals), 400 ppm of NaCl (Wako Pure Chemicals), 250 ppm of $MgCl_2$ (Wako Pure Chemicals), 75 ppm of $CaCl_2$ (Wako Pure Chemicals), and 0.3 ppm of $FeSO_4$ (Wako Pure Chemicals) were prepared, and autoclave sterilization was carried out with a SILICOSEN (glucose was separately sterilized and aseptically mixed in order to avoid Maillard reaction).

First, one loopful of *Bacillus simplex* NBRC15720 strain was taken from a colony grown on a nutrient agar plate, aseptically inoculated into the medium described in the medium condition 1 in Table 1 and cultured overnight with shaking at 37° C. and 150 rpm to obtain a preculture medium.

Three milliliters from the obtained preculture medium was aseptically inoculated into various media described in Table 1 and cultured overnight with shaking at 37° C. and 150 rpm for 40 hours to 72 hours to obtain a culture medium.

After cultivation, the bacterial cell concentration in the culture medium and the sporulation rate of the bacterial cells were measured using an optical microscope and a bacterial cell counter.

Methods for measuring bacterial cell concentration, spore concentration and sporulation rate are as follows. The *Bacillus* simpler strain grown in the culture medium was diluted with, for example, sterile water containing 0.01% Tween 20, and then the bacterial cell concentration (vegetative cells and spores) and the spore concentration were counted with a bacterial cell counter. The sporulation rate was calculated by: spore concentration/bacterial cell concentration.

The C/N ratio was calculated from the weight ratio of the carbon content to the nitrogen content in each medium component. C/N ratio=total carbon content in each media component/total nitrogen content in each media component.

The carbon content in each medium component was calculated by determining the reducing sugar concentration by Somogyi method after hydrolysis in acid and subsequently multiplying the total sugar amount by 0.4.

The nitrogen content in each medium component was determined by the Kjeldahl method.

The potassium content in each medium component was determined by atomic absorption spectrophotometry (measurement wavelength: 766.5 nm).

TABLE 1

Medium composition

| Medium conditions | g/L Glucose | Defatted soy flour | Yeast extract | CSL | Peptone | $KH_2PO_4$ |
|---|---|---|---|---|---|---|
| 1 | 4 | 4.0 | 1.6 | 0.8 | 1.6 | 2.0 |
| 2 | 10.0 | 4.0 | 1.6 | 0.8 | 1.6 | 2.0 |
| 3 | 9.0 | 4.0 | 1.6 | 0.8 | 1.6 | 2.0 |
| 4 | 8.0 | 4.0 | 1.6 | 0.8 | 1.6 | 2.0 |
| 5 | 6.0 | 4.0 | 1.6 | 0.8 | 1.6 | 2.0 |
| 6 | 5.5 | 4.0 | 1.6 | 0.8 | 1.6 | 2.0 |
| 7 | 1.5 | 4.0 | 1.6 | 0.8 | 1.6 | 2.0 |
| 8 | 0.0 | 4.0 | 1.6 | 0.8 | 1.6 | 2.0 |
| 9 | 4.0 | 4.0 | 1.6 | 0.8 | 1.6 | 5.5 |
| 10 | 4.0 | 4.0 | 1.6 | 0.8 | 1.6 | 1 |
| 11 | 4.0 | 4.0 | 1.6 | 0.8 | 1.6 | 0 |
| 12 | 10.0 | 10.0 | 4.0 | 2.0 | 4.0 | 5.0 |
| 13 | 10.0 | 10.0 | 4.0 | 2.0 | 4.0 | 1.0 |
| 14 | 0.5 | 4.0 | 1.6 | 0.8 | 1.6 | 6.4 |
| 15 | 10 | 4.0 | 1.6 | 0.8 | 1.6 | 6.4 |
| 16 | 10 | 4.0 | 1.6 | 0.8 | 1.6 | 0 |
| 17 | 4 | 2.5 | 3.0 | 2.0 | 0 | 1.0 |
| 18 | 4 | 6.0 | 0 | 0 | 0 | 1.0 |

The results are shown in Table 2. At the C/N ratio of 9.5 or more, although growth of the bacterial cells was observed, a decrease in the sporulation rate was detected. On the other hand, at the C/N ratio of 4.0 or less, although growth of the bacterial cells was observed, a decrease in the sporulation rate was detected. The preferred potassium content was found to be in the range of 0.2 to 1.9 g/L.

Example 2

Evaluation of *Bacillus simplex* NBRC104473 Strain

Using a 500 ml Erlenmeyer flask, each 100 ml of media containing glucose (Wako Pure Chemicals), defatted soy flour (Ajinomoto Healthy Supply), yeast extract (Difco), CSL (ROQUETTE), peptone (Difco), and $KH_2PO_4$ (Wako Pure Chemicals) so that the final concentrations of medium conditions 1 to 3 listed in Table 3 were achieved and each further containing 100 ppm of $MnCl_2$ (Wako Pure Chemicals), 400 ppm of NaCl (Wako Pure Chemicals), 250 ppm of $MgCl_2$ (Wako Pure Chemicals), 75 ppm of $CaCl_2$ (Wako Pure Chemicals), and 0.3 ppm of $FeSO_4$ (Wako Pure Chemicals) were prepared, and autoclave sterilization was carried out with a SILICOSEN (glucose was separately sterilized and aseptically mixed in order to avoid Maillard reaction).

One loopful of *Bacillus simplex* NBRC104473 strain was taken from a colony grown on a nutrient agar plate, aseptically inoculated into the medium described in the medium condition 1 listed in Table 3 and cultured overnight with shaking at 37° C. and 150 rpm to obtain a preculture medium. Each 3 ml from the obtained preculture medium used for culturing the *Bacillus simplex* NBRC104473 strain was aseptically inoculated into each medium described in Table 3 and cultured overnight with shaking at 37° C. and 150 rpm for 40 hours to 72 hours to obtain a culture medium. After cultivation, the bacterial cell concentration in the culture medium and the sporulation rate of the bacterial cells were measured using an optical microscope and a bacterial cell counter.

TABLE 3

Medium composition

| Medium conditions | g/L Glucose | Defatted soy flour | Yeast extract | CSL | Peptone | $KH_2PO_4$ |
|---|---|---|---|---|---|---|
| 1 | 4.0 | 4.0 | 1.6 | 0.8 | 1.6 | 2.0 |
| 2 | 0.5 | 4.0 | 1.6 | 0.8 | 1.6 | 6.4 |
| 3 | 10 | 4.0 | 1.6 | 0.8 | 1.6 | 6.4 |

TABLE 2

Culture results for NBRC15720 strain

| Medium condition | Content of each component (g/L) and C/N ratio in medium | | | | Culture result Bacterial cell concentration cell/ml | Sporulation rate % | Spore concentration spore/ml |
|---|---|---|---|---|---|---|---|
| | Potassium content | C/N ratio | Carbon content | Nitrogen content | | | |
| 1 | 0.8 | 6.0 | 4.1 | 0.7 | 2.4E+09 | 75% | 1.8E+09 |
| 2 | 0.8 | 9.5 | 6.5 | 0.7 | 1.6E+09 | 8% | 1.3E+08 |
| 3 | 0.8 | 9.0 | 6.1 | 0.7 | 1.3E+09 | 89% | 1.2E+09 |
| 4 | 0.8 | 8.4 | 5.7 | 0.7 | 1.6E+09 | 89% | 1.5E+09 |
| 5 | 0.8 | 7.2 | 4.9 | 0.7 | 1.6E+09 | 67% | 1.1E+09 |
| 6 | 0.8 | 6.9 | 4.7 | 0.7 | 1.8E+09 | 76% | 1.4E+09 |
| 7 | 0.8 | 4.5 | 3.1 | 0.7 | 1.8E+09 | 70% | 1.3E+09 |
| 8 | 0.8 | 3.7 | 2.5 | 0.7 | 1.1E+09 | 50% | 5.4E+08 |
| 9 | 1.8 | 6.0 | 4.1 | 0.7 | 1.4E+09 | 97% | 1.4E+09 |
| 10 | 0.5 | 6.0 | 4.1 | 0.7 | 2.0E+09 | 90% | 1.8E+09 |
| 11 | 0.2 | 6.0 | 4.1 | 0.7 | 1.2E+09 | 94% | 1.2E+09 |
| 12 | 1.9 | 6.0 | 10.2 | 1.7 | 2.2E+09 | 86% | 1.9E+09 |
| 13 | 0.8 | 6.0 | 10.2 | 1.7 | 2.7E+09 | 82% | 2.2E+09 |
| 14 | 2.0 | 4.0 | 2.7 | 0.7 | 1.3E+07 | 7% | 9.4E+05 |
| 15 | 2.0 | 9.5 | 6.5 | 0.7 | 1.3E+07 | 0% | 0.0E+00 |
| 16 | 0.2 | 9.5 | 6.5 | 0.7 | 1.2E+09 | 25% | 3.1E+08 |
| 17 | 0.5 | 6.5 | 3.5 | 0.4 | 4.0E+09 | 68% | 2.8E+09 |
| 18 | 0.4 | 7.5 | 3.5 | 0.5 | 1.5E+09 | 77% | 1.2E+09 |

The results are shown in Table 4. NBRC104473 strain also showed the same tendency as in Example 1.

TABLE 4

Culture results for NBRC104473 strain

| Medium condition | Content of each component (g/L) and C/N ratio in medium | | | | Culture Bacterial cell concentration cell/ml | result Sporulation rate % | Spore concentration spore/ml |
|---|---|---|---|---|---|---|---|
| | Potassium content | C/N ratio | Carbon content | Nitrogen content | | | |
| 1 | 0.77 | 6.01 | 4.09 | 0.68 | 1.2E+09 | 100% | 1.2E+09 |
| 2 | 2.03 | 3.95 | 2.69 | 0.68 | 4.4E+07 | 0% | 0.0E+00 |
| 3 | 2.03 | 9.54 | 6.49 | 0.68 | 3.2E+07 | 0% | 0.0E+00 |

Example 3

Evaluation in Jar Fermentation System

Using a 5 L culture tank, each 2,000 ml of media containing glucose (Wako Pure Chemicals), defatted soy flour (Ajinomoto Healthy Supply), yeast extract (Difco), CSL (ROQUETTE), peptone (Difco), and KH$_2$PO$_4$ (Wako Pure Chemicals) so that the final concentrations of medium conditions 1 to 3 listed in Table 5 were achieved and each further containing 100 ppm of MnCl$_2$ (Wako Pure Chemicals), 400 ppm of NaCl (Wako Pure Chemicals), 250 ppm of MgCl$_2$ (Wako Pure Chemicals), 75 ppm of CaCl$_2$ (Wako Pure Chemicals), and 0.3 ppm of FeSO$_4$ (Wako Pure Chemicals) were prepared, and autoclave sterilization was carried out (glucose was separately sterilized and aseptically mixed in order to avoid Maillard reaction).

One loopful of *Bacillus simplex* NBRC15720 was taken from a colony grown on a nutrient agar plate, aseptically inoculated into the medium of medium condition 1 described in Example 1 (Table 1) prepared in a 500 ml Erlenmeyer flask and cultured overnight with shaking at 37° C. and 150 rpm to obtain a preculture medium. Each 60 ml from the obtained preculture medium used for culturing the *Bacillus simplex* NBRC15720 strain was aseptically inoculated into each medium described in Table 5 and cultured overnight with aeration and agitation at 37° C. and 400 rpm for 40 hours to obtain a culture medium. After cultivation, the bacterial cell concentration in the culture medium and the sporulation rate of the bacterial cells were measured using an optical microscope and a bacterial cell counter.

TABLE 5

| Medium composition | | | | | | |
|---|---|---|---|---|---|---|
| Medium conditions | g/L Glucose | Defatted soy flour | Yeast extract | CSL | Peptone | KH$_2$PO$_4$ |
| 1 | 10.0 | 10.0 | 12.0 | 8.0 | 0 | 1.0 |
| 2 | 20.0 | 16.0 | 12.0 | 8.0 | 0 | 1.0 |
| 3 | 35.0 | 20.0 | 12.0 | 8.0 | 0 | 0 |

The results are shown in Table 6. As long as C/N is within a certain range, 50% or more of sporulation rate of the *Bacillus simplex* NBRC15720 strain was obtained even in a jar fermentation system.

TABLE 6

Culture results for NBRC15720 strain (jar fermentation system)

| Medium condition | Content of each component (g/L) and C/N ratio in medium | | | | Culture Bacterial cell concentration cell/ml | result Sporulation rate % | Spore concentration spore/ml |
|---|---|---|---|---|---|---|---|
| | Potassium content | C/N ratio | Carbon content | Nitrogen content | | | |
| 1 | 1.24 | 5.41 | 11.67 | 2.16 | 9.0E+09 | 60% | 5.4E+09 |
| 2 | 1.36 | 6.68 | 17.53 | 2.62 | 1.5E+10 | 53% | 7.9E+09 |
| 3 | 1.15 | 8.45 | 24.76 | 2.93 | 1.8E+10 | 61% | 1.1E+10 |

Example 4

Evaluation of *Bacillus siamensis* in Jar Fermentation System

Using a 5 L culture tank, each 2,000 ml of media containing glucose (Wako Pure Chemicals), defatted soy flour (Ajinomoto Healthy Supply), yeast extract (Difco), CSL (ROQUETTE), peptone (Difco), and $KH_2PO_4$ (Wako Pure Chemicals) so that the final concentrations of medium conditions 1 to 3 listed in Table 7 were achieved and each further containing 100 ppm of $MnCl_2$ (Wako Pure Chemicals), 400 ppm of NaCl (Wako Pure Chemicals), 250 ppm of $MgCl_2$ (Wako Pure Chemicals), 75 ppm of $CaCl_2$ (Wako Pure Chemicals), and 0.3 ppm of $FeSO_4$ (Wako Pure Chemicals) were prepared, and autoclave sterilization was carried out (glucose was separately sterilized and aseptically mixed in order to avoid Maillard reaction).

One loopful of *Bacillus siamensis* was taken from a colony grown on a nutrient agar plate, aseptically inoculated into the medium of medium condition 1 described in Table 7 prepared in a 500 ml Erlenmeyer flask and cultured overnight with shaking at 37° C. and 150 rpm to obtain a preculture medium. Each 60 ml from the obtained preculture medium used for culturing the *Bacillus siamensis* was aseptically inoculated into various media described in Table 7 and cultured overnight with aeration and agitation at 37° C. and 400 rpm for 40 hours to obtain a culture medium. After cultivation, the bacterial cell concentration in the culture medium and the sporulation rate of the bacterial cells were measured using an optical microscope and a bacterial cell counter.

TABLE 7

| Medium conditions | Medium composition g/L Glucose | Defatted soy flour | Yeast extract | CSL | Peptone | $KH_2PO_4$ |
|---|---|---|---|---|---|---|
| 1 | 8.0 | 5.0 | 6.0 | 4.0 | 0 | 0.5 |
| 2 | 24.0 | 15.0 | 18.0 | 12.0 | 0 | 0.8 |
| 3 | 36.0 | 15.0 | 18.0 | 12.0 | 0 | 0.8 |

The results are shown in Table 8. As long as C/N is within a certain range, 88% or more of sporulation rate of the *Bacillus siamensis* was obtained even in a jar fermentation system.

TABLE 8

Culture results for *Bacillus siamensis* (jar fermentation system)

| Medium condition | Content of each component (g/L) and C/N ratio in medium: Potassium content | C/N ratio | Carbon content | Nitrogen content | Culture result: Bacterial cell concentration cell/ml | Sporulation rate % | Spore concentration spore/ml |
|---|---|---|---|---|---|---|---|
| 1 | 0.62 | 6.52 | 7.04 | 1.08 | 3.1E+09 | 93% | 2.9E+09 |
| 2 | 1.64 | 6.52 | 21.11 | 3.24 | 6.8E+09 | 88% | 6.0E+09 |
| 3 | 1.64 | 8.00 | 25.91 | 3.24 | 8.0E+10 | 95% | 7.6E+10 |

Example 5

Culture Results for *Bacillus megaterium* (Jar Fermentation System)

Using a 5 L culture tank, each 2,000 ml of media containing glucose (Wako Pure Chemicals), defatted soy flour (Ajinomoto Healthy Supply), yeast extract (Difco), CSL (ROQUETTE), peptone (Difco), and $KH_2PO_4$ (Wako Pure Chemicals) so that the final concentrations of medium conditions 1 to 3 listed in Table 9 were achieved and each further containing 100 ppm of $MnCl_2$ (Wako Pure Chemicals), 400 ppm of NaCl (Wako Pure Chemicals), 250 ppm of $MgCl_2$ (Wako Pure Chemicals), 75 ppm of $CaCl_2$ (Wako Pure Chemicals), and 0.3 ppm of $FeSO_4$ (Wako Pure Chemicals) were prepared, and autoclave sterilization was carried out (glucose was separately sterilized and aseptically mixed in order to avoid Maillard reaction).

One loopful of *Bacillus megaterium* was taken from a colony grown on a nutrient agar plate, aseptically inoculated into the medium of medium condition 1 described in Table 9 prepared in a 500 ml Erlenmeyer flask and cultured overnight with shaking at 37° C. and 150 rpm to obtain a preculture medium. Each 60 ml from the obtained preculture medium used for culturing the *Bacillus megaterium* was aseptically inoculated into various media described in Table 9 and cultured overnight with aeration and agitation at 37° C. and 400 rpm for 40 hours to obtain a culture medium. After cultivation, the bacterial cell concentration in the culture medium and the sporulation rate of the bacterial cells were measured using an optical microscope and a bacterial cell counter.

TABLE 9

| Medium conditions | Medium composition g/L Glucose | Defatted soy flour | Yeast extract | CSL | Peptone | $KH_2PO_4$ |
|---|---|---|---|---|---|---|
| 1 | 8.0 | 5.0 | 6.0 | 4.0 | 0 | 0.5 |
| 2 | 24.0 | 15.0 | 18.0 | 12.0 | 0 | 0.8 |
| 3 | 36.0 | 15.0 | 18.0 | 12.0 | 0 | 0.8 |

The results are shown in Table 10. As long as C/N is within a certain range, 78% or more of sporulation rate of the *Bacillus megaterium* was obtained even in a bulk culture system.

TABLE 10

| Culture results for *Bacillus megaterium* (jar fermentation system) | | | | | | | |
|---|---|---|---|---|---|---|---|
| | Content of each component (g/L) and C/N ratio in medium | | | | Culture Bacterial cell | result Sporulation | Spore |
| Medium condition | Potassium content | C/N ratio | Carbon content | Nitrogen content | concentration cell/ml | rate % | concentration spore/ml |
| 1 | 0.62 | 6.52 | 7.04 | 1.08 | 2.7E+09 | 78% | 2.1E+09 |
| 2 | 1.64 | 6.52 | 21.11 | 3.24 | 8.4E+09 | 95% | 8.0E+09 |
| 3 | 1.64 | 8.00 | 25.91 | 3.24 | 9.2E+10 | 93% | 8.6E+10 |

The invention claimed is:

1. A method for increasing a spore production in *Bacillus simplex*, the method comprising culturing *Bacillus simplex* with a liquid medium having a C/N ratio (weight ratio of carbon content to nitrogen content) of from 4.5 to less than 9.5, wherein a potassium content in the liquid medium is 1.9 g/L or less.

2. The method of claim 1, wherein the C/N ratio in the liquid medium is from 4.5 to 7.5.

3. The method of claim 1, wherein the C/N ratio in the liquid medium is from 6.0 to 7.5.

4. The method of claim 1, wherein the carbon content in the liquid medium is 50 g/L or less.

5. The method of claim 1, wherein the carbon content in the liquid medium is 25 g/L or less.

6. The method of claim 1, wherein the carbon and nitrogen sources contained in the liquid medium are carbon and nitrogen sources which can be utilized by *Bacillus simplex*.

7. The method of claim 6, wherein the carbon source which can be utilized by *Bacillus simplex* is one or more carbon sources selected from the group consisting of starch, glucose, lactose, glycerol, arabinose, ribose, xylose, galactose, fructose, mannose, inositol, mannitol, sorbitol, glucosamine, N-acetylglucosamine, cellobiose, maltose, sucrose, trehalose, xylitol, alcohols, organic acids, organic salts, and alkanes; and the nitrogen source which can be utilized by *Bacillus simplex* is one or more nitrogen sources selected from the group consisting of soybean-derived components, yeast-derived components, corn-derived components, animal and plant proteins and hydrolysates thereof, and ammonium salts such as ammonium nitrate, ammonium sulfate, ammonium chloride, ammonium acetate, ammonia, sodium nitrate, potassium nitrate, sodium glutamate, urea and the like.

8. The method of claim 1, wherein the liquid medium contains $KH_2PO_4$.

9. The method of claim 1, wherein the liquid medium contains $KH_2PO_4$ in an amount of from 0.5 to 5.5 g/L.

10. The method of claim 1, wherein the liquid medium contains $KH_2PO_4$ in an amount of from 0.5 to 2.0 g/L.

11. The method according to claim 1, wherein the culturing is performed for 40 hours to 72 hours.

* * * * *